US00PP16578P3

(12) United States Plant Patent
Smith

(10) Patent No.: US PP16,578 P3
(45) Date of Patent: May 30, 2006

(54) POMEGRANATE TREE DENOMINATED 'SMITH'

(50) Latin Name: *Punica granatum*
Varietal Denomination: Smith

(76) Inventor: Gregory R. Smith, 1449 S. Pinnacle, Visalia, CA (US) 93292

( * ) Notice: Subject to any disclaimer, the term of this patent is extended or adjusted under 35 U.S.C. 154(b) by 60 days.

(21) Appl. No.: 10/699,307

(22) Filed: Oct. 30, 2003

(65) Prior Publication Data

US 2005/0097645 P1 May 5, 2005

(51) Int. Cl.
*A01H 5/00* (2006.01)

(52) U.S. Cl. ..... Plt./210
(58) Field of Classification Search ..... Plt./210
See application file for complete search history.

(56) References Cited

PUBLICATIONS

Harris et al. Plant Identification Terminology an Illustrated Glossary. Spring Lake Publishing, 2001, 2 ed., pp 157 and 171.*

* cited by examiner

*Primary Examiner*—Anne Marie Grunberg
*Assistant Examiner*—June Hwu
(74) *Attorney, Agent, or Firm*—Worrel & Worrel

(57) ABSTRACT

A new and distinct variety of pomegranate tree which is somewhat remotely similar to the 'Granada' pomegranate tree (U.S. Plant Pat. No. 2,618), but from which it is distinguished by producing fruit which are mature for harvesting and shipment approximately September 11 and in which the fruit is of higher acid content when ripe, producing more juice and arils that are moderate red to deep red coloration and softer chewability than those of the fruit of other pomegranate varieties.

1 Drawing Sheet

Latin name of the genus and species of the plant claimed: *Punica granatum* L.
Variety denomination: 'Smith'.

BACKGROUND OF THE NEW VARIETY

The present invention relates to a new and distinct variety of pomegranate tree, which will hereinafter be denominated varietally as the 'Smith' pomegranate tree, and, more particularly, to a pomegranate tree somewhat similar to the 'Granada' pomegranate tree (U.S. Plant Pat. No. 2,618), but which produces fruit with a higher acid content. The new variety of the present invention was discovered as a volunteer seedling growing approximately fifty (50) feet from a 'Granada' pomegranate tree commercial planting. The fruit of the variety of the present invention are mature for commercial harvesting and shipment approximately September 11, or three (3) weeks prior to the 'Wonderful' pomegranate tree (unpatented) in the San Joaquin Valley of central California. The fruit is distinguished from the 'Early Foothill' pomegranate tree, having a redder skin coloration, more juice, higher content when mature (1.85%), and softer arils which are easily chewable.

The sales appeal of pomegranates is generally dependent on size and exterior coloration of the fruit. The acceptability of the pomegranate is also influenced by the color of the edible arils, as well as the acid content and flavor of these arils. One other factor that makes the pomegranate more appealing is that it ripens at a time when other fruits of that general type are not available in the marketplace.

The flavor of the fruit of the new variety is directly related to the acid content when fully ripe. The State of California marketing regulations requires that pomegranate fruit may not be marketed until the acid content of the arils, established by titration is 1.85 percent or less. The aril content of this variety reaches this level by approximately September 11. The rind color of the new variety is close to that of the 'Granada' pomegranate tree (U.S. Plant Pat. No. 2,618) and is Afghan (P1.5L6) in color, rather than on the pink side. When the fruit of the new variety is cut in cross section, the majority of the arils are found to be of a moderate red to strong red coloration. The texture of the arils of the mature fruit of the new variety is such that they can easily be chewed and softer than the arils of other pomegranate varieties, such as, for example, the 'Early Wonderful' pomegranate tree, the 'Granada' pomegranate tree and the 'Early Foothill' pomegranate tree.

ORIGIN AND ASEXUAL REPRODUCTION OF THE NEW VARIETY

The present variety of pomegranate tree hereof was discovered by the inventor in his orchard which is located near Visalia in the San Joaquin Valley of central California.

The new variety of pomegranate tree was first observed by the inventor about four (4) years ago in 1996 growing as a volunteer seedling, approximately fifty (50) feet from a commercial planting of 'Granada' pomegranate trees. In 1998, the seedling was allowed to produce bloom and fruit. The inventor observed that the rind color of the fruit and maturity date resembled the 'Granada' pomegranate tree, but was a heavier juice producer and the arils were significantly softer at maturity. Fruiting bud wood of the new variety has been to asexually reproduce the new variety by grafting on some established 'Granada' pomegranate trees. Such asexually reproduction took place at 19836 Road 196 in Strathmore, Calif. in the United States of America. In addition, a number of rooted hard cuttings were made from the original tree. All of the asexually reproduced trees of the new variety have been observed by the inventor to possess fruit and tree characteristics identical to those of the original tree. The original tree of the instant variety is ten (10) years old. The claimed cultivar is stable and reproduces true to type in successive generations of asexual reproduction.

SUMMARY OF THE INVENTION

The 'Smith' pomegranate tree is characterized by producing a fruit which is ripe for commercial harvesting and shipment approximately September 11 in the San Joaquin Valley of central California. The new variety is most closely similar to the 'Granada' pomegranate tree (U.S. Plant Pat. No. 2,618) and has an exterior color roughly similar to the fruit of that variety, but is distinguishable therefrom in numerous respects including by the aforementioned ripening date.

The new variety is also distinguished from the 'Dutton' pomegranate tree (U.S. Plant Pat. No. 4,826). In describing the axillary angle, the angle between the stems and the fruiting branches of the tree measured from 55 degrees to 62 degrees with the average being 60 degrees for the new variety as compared to the 'Dutton' pomegranate tree averaging 59.2 degrees.

BRIEF DESCRIPTION OF THE DRAWING

The accompanying drawing is a color photograph of four whole fruit of the new variety disposed to display the ventral surface, the basal end surface, and the blossom end surface, a fifth fruit of the new variety sectioned to display the interior thereof, foliage of the new variety, a number of arils thereof together with a scale to indicate relative size.

DETAILED BOTANICAL DESCRIPTION

Referring more specifically to the botanical details of this new and distinct variety of pomegranate tree, the following has been observed under the ecological conditions prevailing in the Strathmore area of Tulare County in the San Joaquin Valley of central California. All major color code designations are by reference to the *Dictionary of Color,* by Maerz and Paul, First Edition, 1930. Common color names are also occasionally employed.

TREE

Generally:

*Size.*—Medium, normal for pomegranates. Ten feet high (3.28 meters).
*Vigor.*—Good.
*Spread.*—Approximately ten (10) feet.
*Chilling requirements.*—Normal for pomegranate.
*Figure.*—Globular/bush.
*Productivity.*—Good, 3 to 4 field box/tree.
*Regularity of bearing.*—Not alternate but will vary with cultural weather conditions.

Trunk:

*Size.*—Multiple, with scaly bark, approximately 10 inch (25.4 cm) diameter and at least 4 feet (1.31 meters) in length. This measurement is of a tree of ten (10) years of age measured two (2) feet from the ground.
*Surface texture.*—Shaggy or scaly.
*Color.*—Brownish Manan (P1. 6 A9).
*Lenticels.*—Numbers — Numerous.
*Lenticels.*—Size — Small.

Branches:

*Size.*—Fruiting wood — 1 inch (2.54 cm) diameter.
*Surface texture.*—Smooth.
*Color.*—Mature branches — Moss Green (P1. 21 L2) with tan ribs.
*Color.*—Immature branches — Brown Sugar (P1. 15 4H).
*Surface texture.*—Immature growth — Smooth.
*Lenticels.*—Numbers — Numerous. The lenticels average ninety-four (94) per one inch of branch where the branch measures three-quarters (¾) of an inch in diameter. [The angle between the stems and branches of the twigs is closer to the 'Granada' pomegranate tree].
*Lenticels.*—Size — Small. The average size of the lenticels is one-sixteenth (1/16) of an inch and they are generally oblong in shape.

The trunk is multiple on the parent tree with a scaffold branch extending from the main trunk at a height of about three (3) feet from the ground and measuring about five (5) inches in diameter. From the scaffold branches, wood is extended which is about one (1) inch in diameter graduating to smaller diameters in the fruiting wood. The color of the trunk is light brown with darker color of brownish gray on the loose bark. More specifically, the trunk color is Brownish Manon (P1. 6 A9) while the branches have an olive green coloration interrupted by brownish lenticels. All branches of the tree of the instant variety are generally round in shape.

LEAVES

Size:

*Generally.*—Small.
*Average length.*—45.8 mm (1.80 inches).
*Average width.*—15.8 mm (0.62 inches).
*Shape.*—Long, oval.

The surface of the leaf has a smooth appearance without hairs, rough texture, or any other characteristics that would deviate from a smooth appearance. The apex of the leaf comes to a tapered point and the base shape of the leaf is rounded.

*Color.*—Upwardly disposed surface — Mt. Vernon Green (P1. 23 J8).
*Color.*—Downwardly disposed surface — Piquant Green (P1. 20 K6).
*Marginal form.*—Generally — Smooth. The entire marginal form of the leaf is smooth.
*Glandular characteristics.*—None.
*Petiole.*—Size — Short. 2 mm (0.079 inches) to 3 mm (0.12 inches).
*Petiole.*—Length — 2 mm (0.079 inches) to 3 mm (0.12 inches).
*Petiole.*—Thickness — Very thin. 1.5 mm (0.07 inches).
*Stem glands.*—None.
*Stipules.*—Mostly two.

Spines are located approximately two (2) inches apart on second ($2^{nd}$) year old wood. They are located in sets of pairs with the spines being positioned across from each other. They vary in size from one-eighth (⅛) inch in length to three and one half (3½) inches in length.

FLOWERS

*Flower buds.*—Generally — Smaller than 'Wonderful' variety.
*Flower buds.*—Size — Length — 10 mm (0.39 inches) to 17 mm (0.76 inches).
*Flower buds.*—Size — Width — 6 mm (0.23 inches) to 12 mm (0.47 inches).
*Flower buds.*—Surface Texture — Smooth, slightly waxy.
*Flower buds.*—Color — Barberry (P1. 5 L7).
*Flower buds.*—Shape — Slightly elongated 10 mm (0.39 inches) to 17 mm (0.69 inches) in length.
*Date of bloom.*—May 15$^{th}$ to May 21$^{st}$ (100%).
*Flowers.*—Number — Single.
*Size.*—Generally — 37 mm (1.44 inches) to 42 mm (1.65 inches) in diameter.
*Petals.*—Color — Barberry (P1. 5 L7).
*Petals.*—Number — Five to seven.
*Pistils.*—Number — One.
*Pistils.*—Size — Length — 10 mm (0.39 inches).
*Stamens.*—Number — Average on hundred and ten (110) per flower.
*Anther.*—Small. The average length of the anthers is two (2) mm.
*Anther.*—Color — Tourquet (P1. 4 B8).
*Filament.*—Color — Red.
*Sepals.*—Number — Five to seven.

FRUIT

Maturity when described: Ripe for commercial harvesting and shipment approximately September 11, three (3) weeks before 'Wonderful' pomegranate tree near Strathmore, Calif. in the San Joaquin Valley of central California.

Size:
*Generally.*—Fairly uniform shape, globular.
*Average diameter.*—79.25 mm (3.42 inches).
*Average diaxial length.*—71.5 mm (2.81 inches).
*Form.*—Typical pomegranate shape, prominent crown of calyx segments at apex, symmetrical base, slightly flattened near stem end.
*Form.*—Uniformity — Fairly uniform — globular.
*Form.*—Symmetry — Individual fruit symmetrical (globular shape).
*Suture.*—Generally — Shallow to none.
*Ventral surface.*—Generally — N/A.

The calyx forms a definite crown on the apex. The points on the calyx number six (6) per piece of fruit. The calyx stays pointed and upright more that a flaring pattern.

*Stem.*—Very short, 6 mm (0.236 inches) with caliper about the same.
*Stem cavity.*—Generally — None.
*Stem.*—Caliper — Approximately 6 mm (0.236 inches).
*Rind.*—Texture — Hard, corky and tough.
*Tendency to crack.*—Late after rains.
*Exterior color.*—Afghan (P1. 5 L6).
*Partition color.*—Maise (P1. 10 G5).
*Aril.*—Color — Azalea (P1. 4 I3) to clear.
*Seed.*—The average length of the seed is one (1) cm by one half (½) cm in diameter. The shape of the seed is more rounded at one end than the other. The rounded end has most of the red coloration. The endocarp in the arils is very soft and very minor if at all noticeable. Comparing the endocarp of the instant variety to that of other known varieties, such as the 'Wonderful,' the 'Early Foothill' and the 'Granada,' there is a distinct and noticeable difference in the eating quality. The endocarp in the instant variety dissolves completely without a residue left. The other aforementioned varieties have a hard endocarp that is noticeable and hard to chew.

Skin:
*Texture.*—Tough.
*Tendency to crack.*—After any fall rains.
*Blush color.*—Exterior — Afghan (P1. 5 L6).

Flesh:
*Flesh color.*—Aril. Moderate red to strong red color.
*Juice production.*—Excellent. Plentiful, sweet with typical pomegranate color and grenadine flavor.
*Flavor.*—Good. Sweet/grenadine.
*Aroma.*—Slight. None.
*Acidity.*—1.55% by September 11.
*Rind texture.*—Tough.
*Fibers.*—Numbers — None.
*Ripening.*—Even.
*Eating quality.*—Very good, good flavor and good juice production, significant acidity with sugar and distinctive grenadine flavor.
*Base.*—Fresh market and juice extract.

Use: Fresh market and juice manufacturer.
Keeping quality: Good.
Resistance to disease: Similar to resistance of 'Granada' variety (U.S. Plant Pat. No. 2,618).
Harvesting: At maturity — beginning Sep. 11, 2000.

Although the new variety of pomegranate tree possesses the described characteristics noted above as a result of the growing conditions prevailing near Strathmore in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of tree, what I claim as new and desire to be secured by Plant Letters Patent is:

1. A new and distinct variety of pomegranate tree substantially as illustrated and described which bears fruit having a deep red rind coloration, arils of color from moderate red to deep red color and with the texture of the arils of the mature fruit easily chewable, being softer than other pomegranate varieties and which has a higher acid content than the fruit of the 'Granada' pomegranate tree at maturity and which ripens for harvesting and shipment approximately September 11 in the San Joaquin Valley of central California.

* * * * *

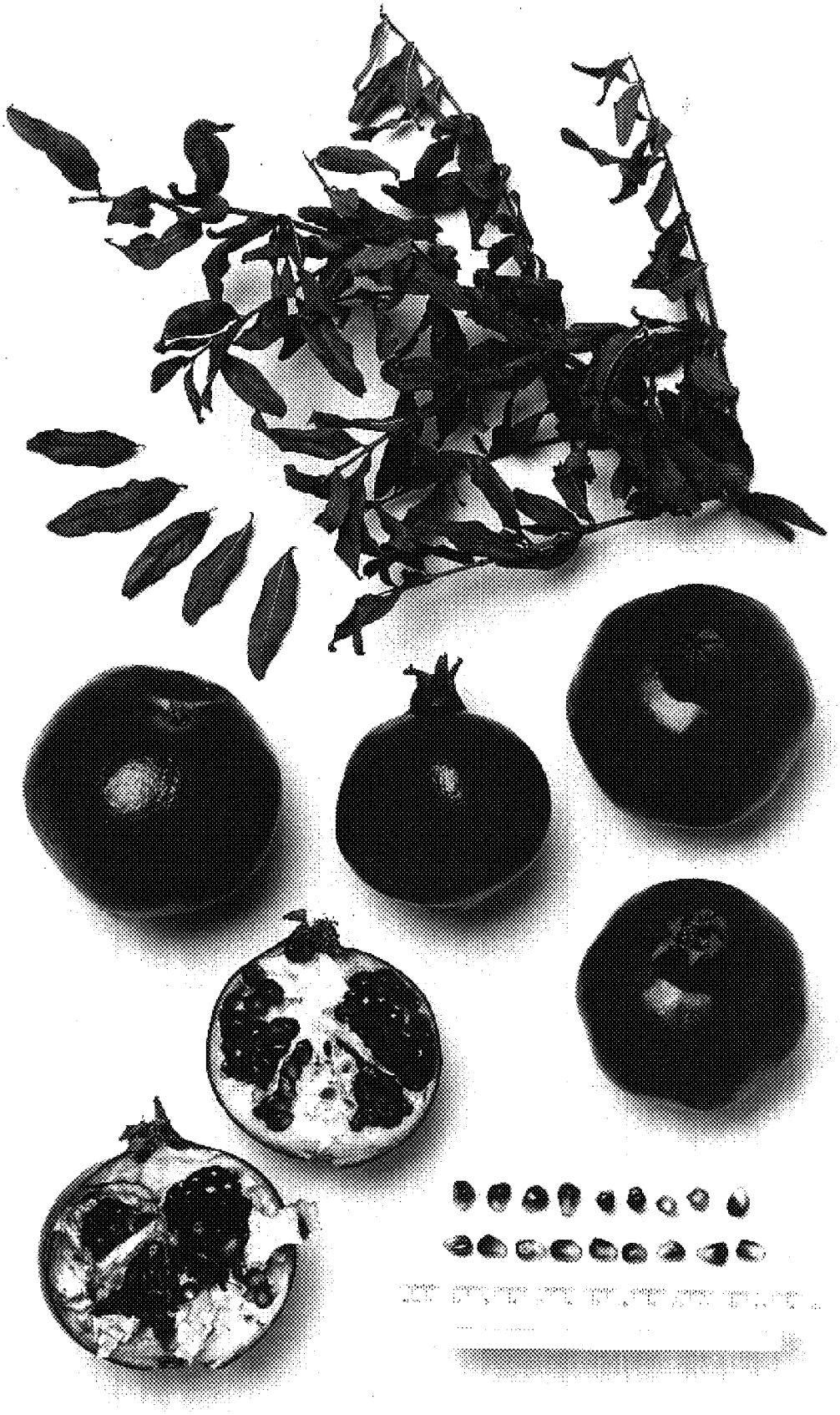

UNITED STATES PATENT AND TRADEMARK OFFICE

CERTIFICATE OF CORRECTION

PATENT NO. : PP 16,578 P3
APPLICATION NO. : 10/699307
DATED : May 30, 2006
INVENTOR(S) : Gregory R. Smith It is certified that error appears in the above-identified patent and that said Letters Patent is hereby corrected as shown below:

Column 1, line 10, after "content" insert --, better flavor and anrils which are more chewable, among other distinctions-- line 20, after "higher" insert --acid--.

Signed and Sealed this

Twenty-second Day of August, 2006

JON W. DUDAS
*Director of the United States Patent and Trademark Office*